United States Patent [19]

Chen

[11] Patent Number: 5,284,607
[45] Date of Patent: Feb. 8, 1994

[54] PROCESS FOR FORMING POWDER-FREE MEDICAL GLOVES

[75] Inventor: Mao-Ching Chen, Arlington, Tex.

[73] Assignee: Johnson & Johnson Medical, Inc., Arlington, Tex.

[21] Appl. No.: 797,517

[22] Filed: Nov. 22, 1991

[51] Int. Cl.$^5$ .................. B29C 41/14; B29C 41/22
[52] U.S. Cl. .................. 264/37; 264/130; 264/232; 264/233; 264/255; 264/306; 264/307
[58] Field of Search .......... 264/233, 215, 216, 305, 264/306, 307, 37, 130, 232, 255

[56] References Cited

U.S. PATENT DOCUMENTS

| | | | |
|---|---|---|---|
| 2,525,272 | 10/1950 | Rhoton | 264/307 |
| 2,950,504 | 8/1960 | Suzuki | 264/307 |
| 3,098,755 | 7/1963 | Barth et al. | 264/307 |
| 3,689,613 | 9/1972 | Talalay | 264/307 |
| 4,061,709 | 12/1977 | Miller et al. | 264/307 |
| 4,143,109 | 3/1979 | Stockum | 264/308 |
| 4,499,154 | 2/1985 | James et al. | 428/494 |
| 5,088,125 | 2/1992 | Ansell et al. | 2/167 |

*Primary Examiner*—Jan H. Silbaugh
*Assistant Examiner*—A. Y. Ortiz
*Attorney, Agent, or Firm*—James Riesenfeld

[57] ABSTRACT

A process for making powder-free medical gloves that are nevertheless easy to don involves first forming a glove on a form by successively dip-coating layers of a coagulant containing acid-soluble powder dispersed throughout, an elastomer, and an antiblocking composition with particles distributed throughout. After curing the elastomer and applying a silicone coating, the glove is removed from the form and treated successively with acid, to dissolve the powder, and with bleach, to reduce blocking. Using this process, high quality natural rubber medical gloves can be produced.

18 Claims, 2 Drawing Sheets

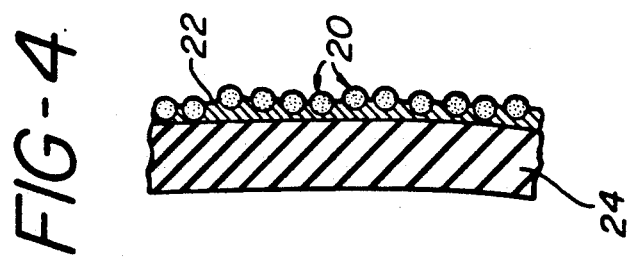
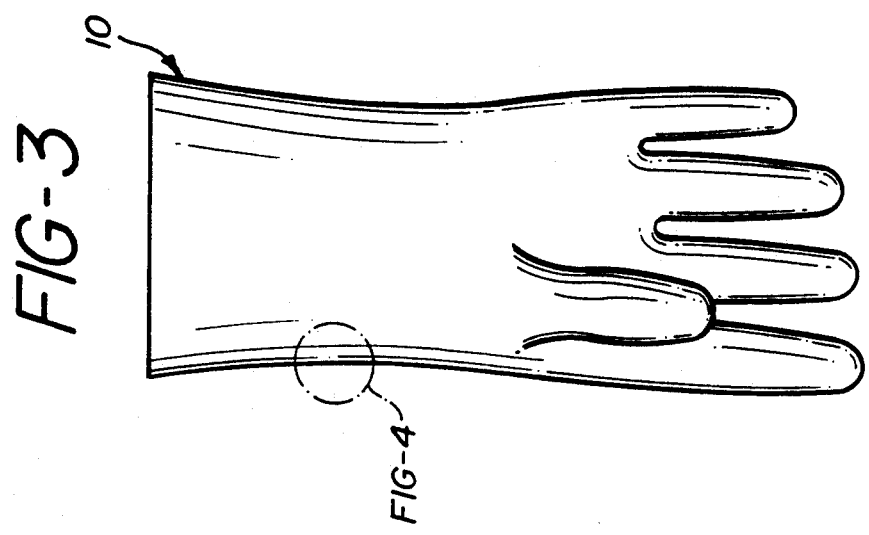
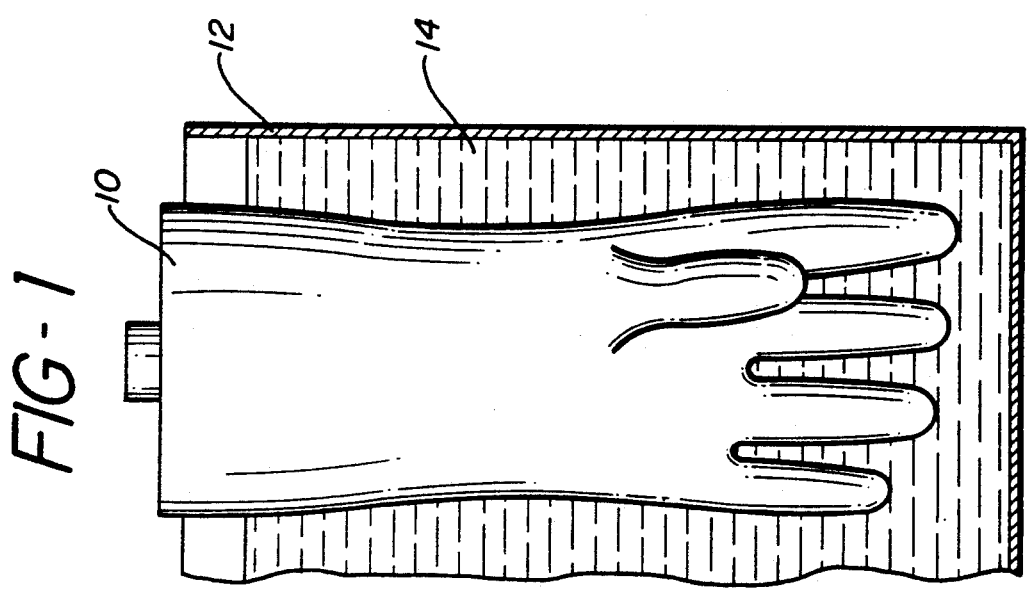

PROCESS FOR FORMING POWDER-FREE MEDICAL GLOVES

BACKGROUND OF THE INVENTION

1. Field of the Invention

This invention relates to a process for making medical gloves that are substantially free of loose powder but are nevertheless easy to don.

2. Description of the Related Art

Medical gloves generally have to conform tightly to the hand of the wearer. That requirement makes it hard to don the gloves, unless they have a lubricant on their inner (skin-contacting) surface. Powder of one form or another has traditionally served this lubricating function; however, post-operative complications, such as adhesions, peritonitis, and granuloma formation have been attributed to the use of loose powder on surgical gloves and other items used in surgery.

To avoid the potential complications, there have long been efforts to reduce or eliminate the need to use powder to facilitate donning of medical gloves. A number of approaches have been tried, including halogenating the gloves, blending rubber and resin latex, and depositing granular material on the inner surface of the gloves. These attempts, and their drawbacks, have been summarized in U.S. Pat. No. 4,143,109, issued on Mar. 6, 1979, to Stockum, and the disclosure of that patent is incorporated herein by reference. Stockum's patent discloses yet another approach to avoiding the need to use loose dusting powder to permit easy donning of gloves. His approach involves having an inner layer of the glove that is bonded to the outer, elastomeric layer. The inner layer has embedded in it particles that are distributed throughout and that are greater in size than the thickness of the inner layer. Thus, the particles protrude from the inner surface, while remaining secured to the surface and not being easily abraded off. A problem with that approach is that the number of particles to be contained in the inner layer has to be carefully controlled. If too few particles are embedded, donning remains difficult. If too many particles are used, some loose particles could remain and could possibly cause the undesirable medical effects.

Another approach to facilitating medical glove donning is disclosed in U.S. Pat. No. 4,499,154, issued on Feb. 12, 1985 to James et al. That approach makes use of a skin-contacting coating of a lubricating hydrogel bonded to the inner surface of the glove and treated with a surfactant to improve its lubricity. However, it is not capable of providing gloves that are as easy to don as powdered gloves.

SUMMARY OF THE INVENTION

In accordance with the present invention, a process for making a powder-free medical glove comprises:

a) forming the glove by
 (i) dip-coating a first layer onto a glove form, the first layer comprising a coagulant with an acid-soluble powder dispersed throughout,
 (ii) dip-coating over the first layer a second layer of an elastomer,
 (iii) dip-coating over the elastomer layer a third layer that comprises an antiblocking composition with particles distributed throughout, the majority of particles having a size greater than the thickness of the antiblocking composition in the third layer,
 (iv) heating the layers to cross-link the elastomer and to bond the elastomer layer to the antiblocking layer, and
 (v) dip-coating a silicone emulsion over the underlying layers;

b) removing the glove from the form and reversing the glove, so that the first layer is on the outside of the glove;

c) treating the glove with an acid to dissolve the acid-soluble powder;

d) rinsing the glove with a first aqueous liquid;

e) treating the glove with a bleach to reduce blocking;

f) rinsing the glove with a second aqueous liquid;

g) treating the glove with a silicone emulsion; and h) drying the glove.

The powder-free medical glove made by this process can be donned without difficulty and has substantially no free powder.

BRIEF DESCRIPTION OF THE DRAWINGS

FIG. 1 depicts a cross section of a tank with a glove form being coated.

FIG. 3 depicts a finished glove.

FIG. 4 shows an enlarged cross section of the glove of FIG. 3.

DETAILED DESCRIPTION OF THE INVENTION

Figure 2:
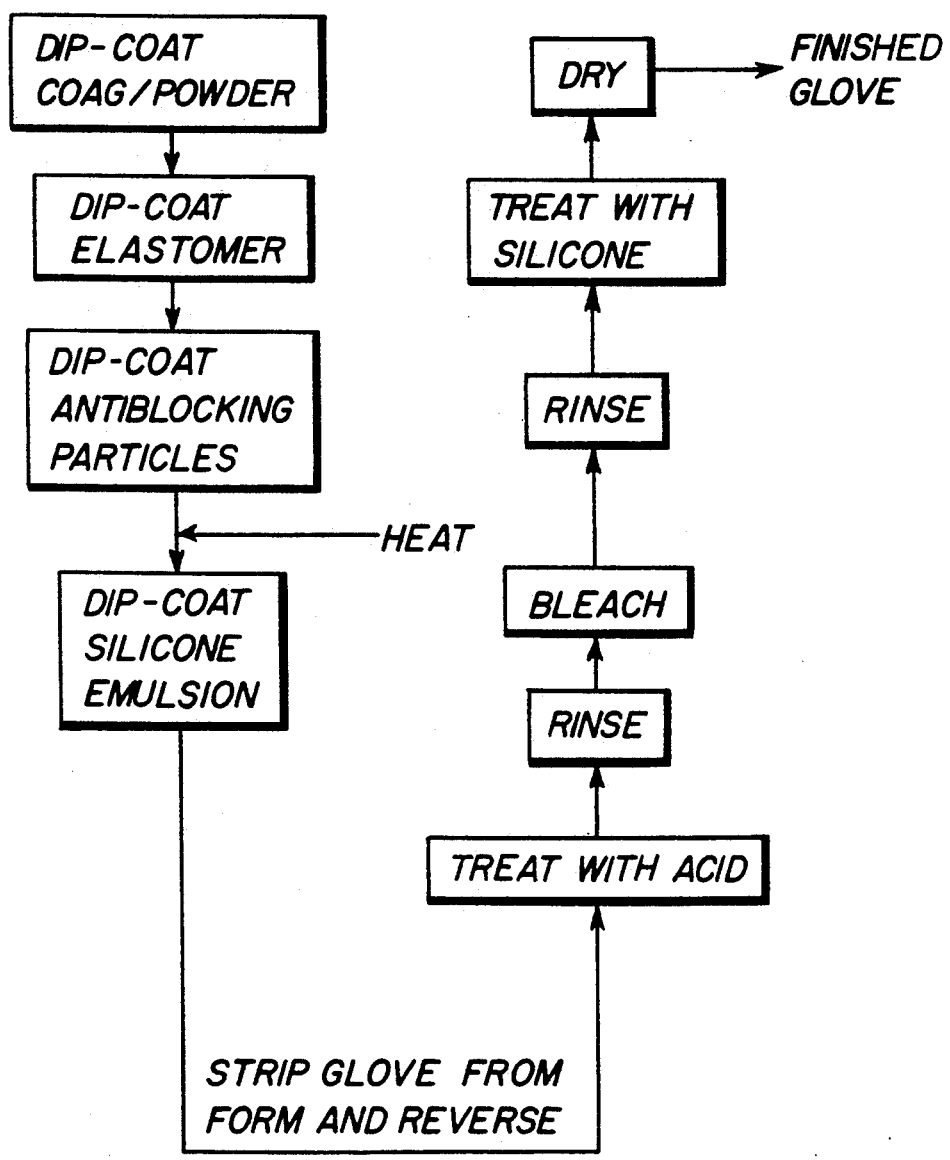
FIG. 2 depicts a flow diagram of the process of the present invention.

The present invention provides a process for making medical gloves that have the combination of properties that are required for these gloves—thin, soft, strong, etc.—and that, in addition, can be donned easily, despite their being powder-free. As used in this specification and the appended claims, "powder-free" means that the gloves contain substantially no loose powder on the completion of the glove-making process.

FIG. 1 illustrates part of an apparatus for practicing the present process. It is of a type that has long been used for making elastomeric gloves and includes a glove form 10, which generally has the shape of a hand, and a tank 12 into which the form is dipped. The complete apparatus includes a series of tanks, each similar to tank 12, into which the form is dipped successively. Of course, the liquid 14 would be different in the different tanks. For dipping purposes, the form 10, the tank 12, or both may be moved. When all the dipping steps are completed, a finished glove is removed, or "stripped", from the form and reversed, so that the first layer is on the outside. The form 10 is generally made of glazed or bisque porcelain or plastic. Of course, the size of the form determines the size of the glove.

Although a variety of elastomers may be used for medical gloves, including natural rubber latex, nitrile rubber latex, coagulable polyurethane aqueous dispersion, and the like, natural rubber latex is preferred because it has superior properties and lower cost. For brevity and convenience, we will describe the process of this invention in the context of natural latex rubber gloves, recognizing that the modifications necessary to produce gloves of other common materials will be clear to the artisan. Conventional methods for preparing latex rubber gloves are described in a bulletin "Dipping With Natural Rubber Latex", The Malaysian Rubber Producers' Research Association, Hertford, England, 1980, and the disclosure of that bulletin is incorporated herein by reference.

In order to provide reproducible latex layers on the form, a coagulant layer is first dipped onto the form. The coagulant may be of any composition well known in the art and described in the above-mentioned bulletin, such as alcohol solutions of calcium salts. The coagulant includes an acid soluble powder, such as calcium carbonate, which will facilitate stripping the glove from the form and will subsequently be dissolved in acid.

The coagulant-coated form is then dipped into latex, after which the latex layer gels. Preferably, the gelled layer is leached in water to extract a large percentage of the water-soluble impurities in the latex and coagulant.

An antiblocking composition with particles distributed throughout is then dip-coated over the latex. "Blocking" refers to the tendency of glove surfaces to stick together. The antiblocking composition, which will be on the interior surface of the glove after stripping, keeps the interior surfaces of the glove from sticking together and making it difficult or impossible to get air and liquids into the fingers for post-strip processing. The antiblocking composition also serves as a binder to bind the particles to the rubber. It should have tensile strength, elongation, tear strength, and modulus that are comparable to that of the natural rubber. Suitable compositions include carboxylated styrene butadiene lattices, carboxylated butadiene acrylonitrile lattices, vinyl acrylate lattice, polyurethane aqueous dispersions, and the like. Polyurethane aqueous dispersion is preferred, because it provides the best combination of mechanical parameters. Especially preferred is a cationic polyurethane having a molecular weight of at least 100,000. Cationic compositions are found to provide desirably softer gloves than anionic or nonionic compositions. The high molecular weight ensures that blocking is complete. Suitable antiblocking compositions include Neorez polyurethane emulsions, such as Neorez XR-9208 (cationic) and Neorez R-962 and R-967 (nonionic/anionic), available from ICI Resins, Wilmington, Mass.

The particles dispersed through the antiblocking composition are larger than the thickness of the antiblocking layer and form protrusions on the inner surface of the glove (after stripping and reversal). The resulting roughened surface enhances the antiblocking effect and facilitates fluid flow into and out of the glove during post-stripping operations. The particles may be any of a variety of acid-resistant compositions, such as cross-linked cornstarch, polyurethane, nylon, or mixtures. A polyester based polyurethane powder is preferred. Such a powder is Vedoc VP180, available from Ferro Corp, Cleveland, Ohio. Also suitable are Corvel nylon powders, available from Morton Chemical Div., Reading, Pa.; and epichlorohydrin cross-linked cornstarch (Vulca 90), available from National Starch and Chemical Corp., Bridgewater, N.J. The particles should have a size in the range from about 5 to about 50 micrometers, preferably having an average particle size of about 30 to about 40 micrometers. Reference to size for purposes of this specification and claims is the diameter, if the particles are spherical, or the diameter of a sphere having the same volume, if the particles are not spherical. Additional facts regarding the particles are described in U.S. Pat. No. 4,143,109, and that description is incorporated herein by reference.

After the antiblocking/particle layer has been deposited, the form with the 3 layers coated on it is heated to cure (i.e., cross-link) the rubber and to bond the rubber to the antiblocking layer. The cure time and temperature are known in the art and are not critical; however, if the temperature is too low, the rubber may be inadequately bonded to the antiblocking layer.

After the layers have been cured, a silicone emulsion is dip-coated over the underlying layers to facilitate donning of the finished glove. The emulsion may also include an acid-soluble powder, which makes stripping easier and which is ultimately dissolved in acid.

The fully-formed glove is then stripped from the form and reversed, so that the first layer is on the outside of the glove. The glove is then treated with an acid to dissolve the acid-soluble powder(s). This acid treatment, which generally takes about five minutes, serves to dissolve loose powder to provide a powder-free glove. The acid treatment, as well as the other post-stripping operations (except for drying), are performed in a conventional front-loading industrial washing machine, such as the UDY75 machine, available from Unimac Co., Inc., Marianna, Fla. The main criterion for an acid suitable for this step is that its calcium salt be water soluble (if the powder is calcium carbonate). Nitric acid is preferred, because all nitrates are water soluble. The preferred nitric acid concentration is in the range from about 0.5% to about 10%. If the acid is too concentrated, it can stain the glove; if it is too dilute, it may not dissolve all the powder. A 2% nitric acid solution is preferred. Before the acid wash, the glove is preferably "pre-washed" in a dilute acid (concentration less than about 1%). The source of the dilute acid may conveniently be spent acid collected from the acid wash cycle.

After the acid wash, the glove is rinsed in an aqueous liquid, e.g., water. It is then treated with a bleach (such as 0.5% sodium hypochlorite) to chlorinate the inner and outer glove surfaces and prevent blocking—e.g., fingers sticking together on a single glove or gloves sticking together when brought into contact. The bleach treatment, which generally takes about fifteen minutes, does not cause the gloves to have the excessively slippery outer surface that the prior art chlorine treatments caused.

The glove is then rinsed with an aqueous liquid—water is again suitable—to remove any residue of bleach, which could otherwise cause skin irritation. Since the post-stripping processes, including acid and bleach treatments, may remove the silicone from the glove surface, there follows a second silicone treatment. This treatment, which generally takes about five minutes, facilitates glove donning and reduces blocking between gloves that come into contact. Finally, the glove is dried in a conventional dryer.

The steps of the present invention are depicted in the flow diagram of FIG. 2.

The appearance of the finished glove is shown in FIG. 3.

FIG. 4 shows an enlarged representative cross section of the glove wall, showing particles 20 embedded in antiblocking inner layer 22, which is bonded to elastomer outer layer 24.

The present invention is further described in the following examples.

EXAMPLE I

A layer of natural rubber latex is applied to an average thickness of 150 micrometers onto a glove form, which then is dipped into the following antiblocking coating formulation:

|  | Parts by Wt. |
| --- | --- |
| NeoRez* XR-9208 | 285.71 |
| Deionized Water | 84.62 |
| Vedoc* VP 180 | 18.00 |

A layer of the formulation is deposited over the layer of natural rubber latex. The layers are then cured and dipped in a dilute silicone emulsion, such as "LE-46" emulsion, produced by Union Carbide Corp. The glove is stripped from the form in a manner that reverses the glove to place the first deposited layer on the outer surface of the glove.

Post-stripping treatment of the powdered gloves to produce a powder-free glove is performed in the following sequence:
1. Pre-wash with a spent acid, which is collected from the acid wash cycle.
2. Wash with 2% nitric acid solution.
3. Rinse with water three times.
4. Treat with 0.5% sodium hypochlorite solution.
5. Rinse with water twice.
6. Treat with 0.25% silicone emulsion.
7. Dry in a dryer.

The glove is found to have no loose powder and has good quality.

EXAMPLE II

In accordance with the general procedure of EXAMPLE I, a glove is produced utilizing the following antiblocking coating formulation:

|  | Parts by Wt. |
| --- | --- |
| NeoRez* XR-9208 | 285.71 |
| Deionized Water | 84.62 |
| Vulca* 90 | 18.00 |

The glove is found to have no loose powder and has good quality.

EXAMPLE III

In accordance with the general procedure of EXAMPLE I, a glove is formed utilizing the following antiblocking coating formulation:

|  | Parts by Wt. |
| --- | --- |
| NeoRez* R-967 | 75.00 |
| NeoRez* R-962 | 205.88 |
| Deionized Water | 266.31 |
| Igepal* CO-630 | 0.20 |
| Vedoc* VP-180 | 17.65 |

Igepal, a surfactant available from GAF Corp., New York, N.Y., facilitates dispersing the Vedoc VP-180 powder. The glove is found to have no loose powder and has good quality.

EXAMPLE IV

In accordance with the general procedure of Example I, a glove is formed utilizing the following antiblocking coating formulation:

|  | Parts by Wt. |
| --- | --- |
| NeoRez* XR-9208 | 285.71 |
| Deionized Water | 150.14 |
| Nylon Powder (Corvel* Natural 78-9001) | 18.00 |

The glove is found to have no loose powder and has good quality.

I claim:
1. A process for making a powder-free medical glove comprising the steps of:
   a) forming the glove by
      (i) dip-coating a first layer onto a glove form, the first layer comprising a coagulant with a first acid-soluble powder dispersed throughout,
      (ii) dip-coating over the first layer a second layer of an elastomer,
      (iii) dip-coating over the elastomer layer a third layer that comprises an antiblocking composition with particles distributed throughout, the majority of particles having a size greater than the thickness of the antiblocking composition in the third layer,
      (iv) heating the layers to cross-link the elastomer and to bond the elastomer layer to the antiblocking layer, and
      (v) dip-coating a silicone emulsion over the underlying layers;
   (b) removing the glove from the form and reversing the glove, so that the first layer is on the outside of the glove;
   (c) treating the glove with an acid to dissolve the acid-soluble powder;
   (d) rinsing the glove with a first aqueous liquid;
   (e) treating the glove with a bleach to reduce blocking;
   (f) rinsing the glove with a second aqueous liquid;
   (g) treating the glove with a silicone emulsion; and
   (h) drying the glove.
2. The process of claim 1 in which the elastomer comprises natural rubber latex.
3. The process of claim 1 in which the antiblocking composition is selected from the group consisting of carboxylated styrene butadiene lattice, carboxylated butadiene lattice, vinyl acrylate lattice, and polyurethane aqueous dispersions.
4. The process of claim 1 in which the antiblocking compound comprises a cationic polyurethane of molecular weight at least about 100,000.
5. The process of claim 1 in which the particles comprise a material selected from the group consisting of cornstarch, polyurethane, nylon, and mixtures thereof.
6. The process of claim 5 in which the particles comprise a polyester based polyurethane powder.
7. The process of claim 1 in which the size of the particles is in the range from about 5 to about 50 micrometers.
8. The process of claim 1 in which the average particle size is about 30 to about 40 micrometers.
9. The process of claim 1 in which the acid-soluble powder comprises calcium carbonate.
10. The process of claim 1 in which the silicone emulsion has a silicone concentration in the range from about 0.05% to 1.5%.
11. The process of claim 10 in which the silicone concentration in the emulsion is in the range from about 0.2% to 0.65%.

12. The process of claim 1 in which the silicone emulsion further comprises a second acid-soluble powder, which is subsequently dissolved by the acid.

13. The process of claim 1 in which the acid comprises nitric acid.

14. The process of claim 13 in which the nitric acid concentration is in the range from about 0.5% to 10%.

15. The process of claim 1 in which the bleach comprises sodium hypochlorite.

16. The process of claim 1 further comprising leaching the first two layers in water to remove soluble impurities before dip-coating the third layer.

17. The process of claim 1 further comprising pre-washing the glove in a dilute acid before treating the glove with acid.

18. The process of claim 17 in which the dilute acid for the pre-wash comprises acid that has been used previously to treat earlier gloves.

* * * * *